United States Patent [19]

Janssen et al.

[11] Patent Number: 4,464,381
[45] Date of Patent: Aug. 7, 1984

[54] FUNGICIDES CONTAINING AZOLYLMETHYLOXIRANES

[75] Inventors: Bernd Janssen, Ludwigshafen; Norbert Meyer, Ladenburg; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 491,650

[22] Filed: May 5, 1983

[30] Foreign Application Priority Data

May 14, 1982 [DE] Fed. Rep. of Germany ....... 3218130

[51] Int. Cl.$^3$ ...................... A01N 43/48; A01N 43/50
[52] U.S. Cl. ................................. 424/269; 424/273 R
[58] Field of Search ................ 548/262, 336; 424/269, 424/273 R

[56] References Cited

U.S. PATENT DOCUMENTS 3,435,049 5/1969 Nutley ............................ 548/336 X
3,468,902 9/1969 Beaman et al. ................. 548/336 X
3,493,582 2/1970 Nutley ................................. 548/336
4,404,216 9/1983 Richardson ........................ 548/262

FOREIGN PATENT DOCUMENTS 2431407 2/1977 Fed. Rep. of Germany .
2249616 5/1975 France .

Primary Examiner—Leonard Schenkman
Assistant Examiner—Joseph A. Lipovsky
Attorney, Agent, or Firm—Keil & Weinkauf

[57] ABSTRACT

Azolylmethyloxiranes of the formula

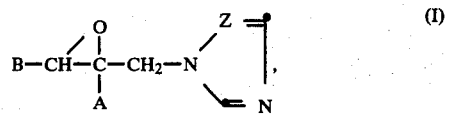

where A and B are identical or different and independently of one another are each alkyl of 1 to 4 carbon atoms, naphthyl, biphenyl or phenyl, and the phenyl radical can be substituted by halogen or nitro, or by alkyl, alkoxy or haloalkyl, each of 1 to 4 carbon atoms, or by phenoxy or phenylsulfonyl, and Z is CH or N, and their plant-tolerated addition salts with acids, and metal complexes, and fungicides containing these compounds.

3 Claims, No Drawings

FUNGICIDES CONTAINING AZOLYLMETHYLOXIRANES

The present invention relates to novel azolylmethyloxiranes, a process for their preparation, and fungicides containing these compounds.

It has been disclosed that azole compounds, eg. azolylmethylcarbinols or azolylmethyl ketones (German Laid-Open Application DOS No. 2,431,407, French Pat. No. 2,249,616) can be used as fungicides. However, their action is unsatisfactory.

We have found that azolylmethyloxiranes of the formula I

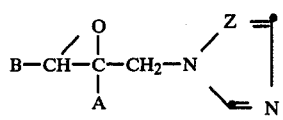

where A and B are identical or different and independently of one another are each alkyl of 1 to 4 carbon atoms, naphthyl, biphenyl or phenyl, and the phenyl radical can be substituted by halogen or nitro, or by alkyl, alkoxy or haloalkyl, each of 1 to 4 carbon atoms, or by phenoxy or phenylsulyfonyl, and Z is CH or N, and their plant-tolerated addition salts with acids, and metal complexes, have good fungicidal actions.

The novel compounds of the formula I possess chiral centers, and are obtained in general in the form of a racemate or as a diastereomer mixture of the erythro and threo forms.

The erythro and threo disastereomers of the novel compounds can be separated, for example, by utilizing differences in solubility or by column chromatography, and can be isolated in pure form. Individual enantiomers can be obtained from such pure diastereomer pairs by a conventional method. The present invention embraces the enantiomers as well as their mixtures (racemates). The pure diastereomers or enantiomers as well as mixtures thereof can be used as fungicides.

A and B are each, for example, methyl, ethyl, propyl, isopropyl, butyl, sec.-butyl, isobutyl, tert.-butyl, naphth-1-yl, naphth-2-yl, p-biphenyl, phenyl, 2-chlorophenyl, 3-chlorophenyl, 4-chlorophenyl, 4-fluorophenyl, 4-bromophenyl, 2,4-dichlorophenyl, 3,4-dichlorophenyl, 3,5-dichlorophenyl, 3-chloro-4-methylphenyl, 2-methoxyphenyl, 3-methoxyphenyl, 2,4-dimethoxyphenyl, 3,4-dimethoxyphenyl, 4-methoxyphenyl, 4-ethoxyphenyl, 4-tert.-butoxyphenyl, 4-methylphenyl, 4-ethylphenyl, 4-isoprophylphenyl, 4-tert.-buthylphenyl, 4-phenoxyphenyl, 3-phenoxyphenyl, 3-nitrophenyl, 4-nitrophenyl, 3-trifluoromethylphenyl, 4-trifluoromethylphenyl and 4-phenyl-sulfonylphonyl.

Examples of addition salts with acids are the hydrochloriedes, bromides, sulfates, nitrates, phosphates, oxalates and dodecylbenzenesulfonates. The activity of the salts is attributable to the cation, and any desired anion may therefore be chosen, non-phytotoxic anions being preferred. The salt is prepared by reacting the azolylmethyloxirane with the appropriate acid. Metal complexes are compounds of the formula

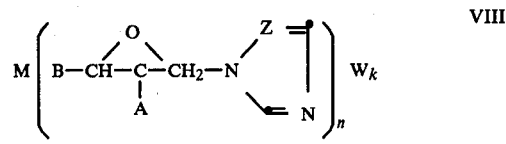

where A, B and X have the above meanings, M is a metal, e.g. copper, zinc, tin, manganese, iron, cobalt or nickel, W is an anion of an inorganic acid, e.g. hydrochloric acid, sulfuric acid, phosphoric acid or hydrobromic acid, and n and k are each 1, 2, 3 or 4. They are prepared by reacting the azolylmethyloxirane with the appropriate metal salt.

The novel fungicidal compounds of the formula I can be prepared by a process wherein an oxirane of the formula II

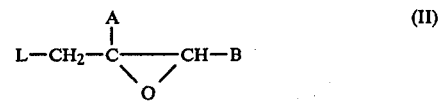

where A and B have the above meanings and L is a leaving group, e.g. chloride, bromine, methylsulfonyloxy or 4-methylphenylsulfonyloxy, which can undergo nucleophilic substitution, is reacted with an azole of the formula III

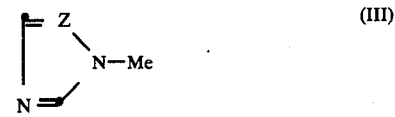

where Me is preferably a metal atom, e.g. sodium or potassium.

The reaction is carried out in the presence or absence of a solvent or diluent, with or without the addition of an inorganic or organic base and with or without the addition of a reaction accelerator at from −10 to 120° C. Preferred solvents and diluents include ketones, e.g. acetone, methyl ethyl kentone and cyclohexanone, nitriles, e.g. acetonitrile, esters, eg. ethyl acetate, ethers, e.g. diethyl ether, tetrahydrofuran and dioxane, sulfoxides, e.g. dimethylsulfoxide, amides, eg. dimethylformamide, dimethylacetamide and N-methylpyrrolidone, and sulfolane, as well as mixtures of these.

Examples of suitable bases, which if appropriate may also be used in the reaction as acid acceptors, are alkali metal hydroxides, e.g. lithium hydroxide, sodium hydroxide and potassium hydroxide, alkali metal carbonates, e.g. sodium carbonate, potassium carbonate, sodium bicarbonate and potassium bicarbonate, an excess of the 1,2,4-triazole, and pyridine and 4-dimethylaminopyridine. However, another conventional base may also be used.

Preferred reaction accelerators are metal halides, e.g. sodium iodide and potassium iodide, quaternary ammonium salts, e.g. tetrabutylammonium chloride, bromide and iodide, and benzyltriethylammonium chloride and bromide, and crown ethers, e.g. 12-crown-4, 15-crown-5, 18-crown-6, dibenzo-18-crown-6 and dicyclohexane-18-crown-6.

The reaction is carried out in general at from −10 to 120° C., under atmospheric or superatmospheric pressure, either continuously or batchwise.

The starting compounds II are novel. They are prepared by expoxidation of an olefin of the formula IX

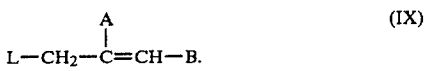

General methods for the synthesis of an oxirane from an olefin are known (e.g. Dittus in Houben-Weyl-Müller, Methoden der organishcen Chemie, George Thieme Verlag, Stuttgart, 1965, Vol. VI, 3, page 385 et seq.).

The olefin IX is oxidized, under the conditions stated in the above publication, or under appropriately modified conditions, with a peroxycarboxylic acid, e.g. perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, e.g. methylene chloride, chloroform, carbon teterachloride or dichloroethane, or if appropriate in acetic acid, ethyl acetate, acetone or dimethylformamide, in the presence or absence of a buffer, e.g. sodium acetate, sodium carbonate, sodium bicarbonate or disodium hydrogen phosphate. The reaction is carried out at from 10° to 100° C., and is catalyzed, if required, for example with iodine or sodium tungstate or by exposure to light. Oxidation may also be carried out using an alkaline solution of hydrogen peroxide (about 30% strength) in methanol, ethanol, acetone or acetonitrile at from 25° to 30° C., or an alkyl hydroperoxide, e.g. tert.-butyl hydroperoxide, with the addition of a catalyst, e.g. sodium tungstate, pertungstic acid, molybdenum carbonyl or vanadyl acetylacetonate. Some of the stated oxidizing agents may be produced in situ.

Mast of the compounds IX are novel. They are prepared by a process wherein an olefin of the formula X

is halogenated or oxidized at the allyl position by a method which is known in principle. A suitable halogenating reagent is N-chlorosuccinimide or N-bromosuccinimide in a halohydrocarbon, e.g. carbon tetrachloride, trichloroethane or methylene chloride, and the reaction is carried out at from 20° to 100° C. Allyl oxidation is carried out using a per-ester, e.g. tert.-butyl perbenzoate or tert.-butyl peracetate, in the presence of a heavy metal salt, e.g. copper(I) chloride or copper(I) bromide, in an inert solvent at from 10° to 100° C.

The compounds X, some of which were unknown hitherto, can be obtained by a conventional method of olefin synthesis (Houben-Weyl-Müller, Methoden der organischen Chemie, George Thieme Verlag, Stuttgart, 1972, Vol. V, 1b).

The resulting compound of the formula I is isolated by a conventional method, purified if required, and if appropriate reacted with an acid to give a salt, or with a metal salt to give a metal complex.

The Examples and Methods which follow illustrate the preparation of the novel compounds and their intermediates.

METHOD 1

63.6 g of potassium tert.-butylate in 300 ml of dry methanol were introduced into a solution of 229 g of 2,4-dichlorobenzyltriphenylphosphonium chloride in 800 ml of dry methanol at 10° C., and 77.2 g of 4-chloroaceto-phenone were added after half an hour. The reaction solution was refluxed for 3 hours, the precipitated salt was filtered off at room temperature, the filtrate was evaporated down under reduced pressure, the residue was digested with petroleum ether at from 50° to 70° C. to free it from triphenylphosphine oxide, and the solution was evaporated down under reduced pressure.

The residue was taken up in 1 liter of carbon tetrachloride, and the solution was refluxed with 81.7 g of N-bromosuccinimide and 4 g of 2,2'-azoisobutyrodinitrile. After the reaction was complete, the succinimide was filtered off, the filtrate was evaporated down under reduced pressure and the residue was recystallized from methanol. 73.4 g (38.8%) of Z-1-(2,4-dichlorophenyl)-2-(4-chlorophenyl)-3-bromoprop-1-ene of melting point 128° C. were obtained.

METHOD 2

118 g of 2,4-dichlorobenzyl chloride were added dropwise to 14.6 g of magnesium turnings in 400 ml of dry diethyl ether at the boiling point. After the reaction was complete, a solution of 77.3 g of 4-chloroacetophenone in 400 ml of dry diethyl ether was added. Thereafter, decomposition was effected with aqueous ammonium chloride solution, the organic phase was separated off, washed neutral, dried over sodium sulfate and evaporated down under reduced pressure, the residue was taken up in 1 liter of toluene and the solution was refluxed with 4 g of 4-methylbenzenesulfonic acid, in a water separator. After dehydration was compelete, the toluene phase was washed with sodium carbonate solution and water and dried over sodium sulfate, the solvent was evaproated off and the residue was recrystallized from methanol to give 107 g (81.9%) of E-1-(2,4-dichlorophenyl)-2-(4-chlorophenyl)-prop-1-ene of melting point 84°-85° C.

METHOD 3

104 g of E-1-(2,4-dichlorophenyl)-2-(4-chlorophenyl)-prop-1-ene were refluxed with 62.3 g of N-bromosuccinimide and 5 g of 2,2'-azoisobutyrodinitrile in 1 liter of carbon tetrachloride, the precipitated succinimide was filtered off and the filtrate was evaporated down under reduced pressure. Treatment of the residue with methanol gives 91.5 g (69.4%) of Z-1-(2,4-dichlorophenyl)-2-(4-chlorophenyl)-3-bromoprop-1-ene of melting point 128° C.

METHOD 4

58.9 g of Z-1-(2,4-dichlorophenyl)-2(4-chlorophenyl)-3-bromoprop-1-ene were refluxed with 52.3 g of 3-choroperoxybenzoic acid in 590 ml of chloroform. After the reaction was complete, the chloroform phase was washed acid-free with aqueous sodium bicarbonate solution and water, dried over sodium sulfate and evaporated down under reduced pressure, and the residue was recrystallized from methanol to give two crystalline fractions:

4.1 41.3 g (70.2%) of 2-bromomethyl-2-(4-chlorophenyl)-3-(2,4-dichlorophenyl)-oxirane (isomer A) of melting point 98°-99° C., and, 4.2 12 g (20.4%) of 2-bromomethyl-2-(4-chlorophenyl)-3-(2,4-dichlorophenyl)-oxirane (isomer B) of melting point 93°-95° C.

EXAMPLE 1

A solution of 10 g of 2-bromomethyl-2-(4-chlorophenyl)-3-(2,4-dichlorophenyl)-oxirane (isomer A) in 50 mL of N,N-dimethylformamide was added dropwise, at 100° C., to a melt which comprised 15.6 g of imidazole with 1.37 g of sodium methylate and from which the liberated methanol had been distilled off beforehand. After 8 hours, the reaction solution was poured onto water and the mixture was extracted with ethyl acetate. The organic phase was washed with water, dried over sodium sulfate and evaporated down under reduced pressure, and the residue was chromatographed over a silica gel column using methylene chloride/methanol (100:2). The purified fractions were evaporated down, and the residue was crystallized from diisopropyl ether. 4.6 g (47.5%) of 2-(1H-imidazol-1-yl-methyl)-2-(4-chlorophenyl)-3-(2,4-dichlorophenyl)-oxirane (isomer A) of melting point 102°–103° C. were obtained (compound 1).

EXAMPLE 2

6.2 g of imidazole and 1.3 g of sodium hydride (50% strength dispersion in mineral oil) were dispersed in 50 ml of N,N-dimethylformamide, and a solution of 12 g of 2-bromomethyl-2-(4-chlorophenyl)-3-(2,4-dichlorophenyl)-oxirane (isomer B) and 5 g of potassium iodide in 50 ml of N,N-dimethylformamide was added at room temperature (20° C.). After 8 hours, the reaction solution was poured onto water and the mixture was extracted with ethyl acetate. The organic phase was washed with water and dried over sodium sulfate, the solvent was evaporated off under reduced pressure and the residue was recrystallized from diisopropyl ether. 9.4 g (82.5%) of 2-(1H-imidazol-1-yl-methyl)-2-(4-chlorophenyl)-3-(2,4-dichlorophenyl)-oxirane (isomer B) of melting point 109° C. were obtained (compound 2).

EXAMPLE 3

20.9 g of 1,2,4-triazole and 4.4 g of sodium hydride (50% strength dispersion in mineral oil) were dispersed in 150 mL of N,N-dimethylformamide, and a solution of 39.2 g of 2-bromomethyl-2-(4-chlorophenyl)-3-(2,4-dichlorophenyl)-oxirane (isomer A) and 16.6 g of potassium iodide in 150 ml of N,N-dimethylformamide was added at room temperature. After 8 hours, the reaction solution was worked up as described in Example 2, and the product was recrystallized from diisopropyl ether. 31 g (81.9%) of 2-(1,2,4-triazol-1-ylmethyl)-2-(4-chlorophenyl)-3-(2,4-dichlorophenyl)-oxirane (isomer A) of melting point 119° C. were obtained (compound 3).

Those compounds which are listed in the Table together with their melting points (mp.) were prepared by a similar procedure. Their structures were established by $^1$H-NMR or $^{13}$C-NMR analysis. The compounds for which no physicochemical data are given can be obtained in the same manner as the compounds actually prepared; they are expected to have actions similar to those of the compounds investigated in more detail, since they possess a similar constitution.

| Ex. no. | A | B | Z | Diastereomer | M.p. [°C.] |
|---|---|---|---|---|---|
| 1 | 4-Cl—$C_6H_4$ | 2,4-$Cl_2$—$C_6H_3$ | CH | A | 102–103 |
| 2 | 4-Cl—$C_6H_4$ | 2,4-$Cl_2$—$C_6H_3$ | CH | B | 109 |
| 3 | 4-Cl—$C_6H_4$ | 2,4-$Cl_2$—$C_6H_3$ | N | A | 119 |
| 4 | 4-Br—$C_6H_4$ | $C_6H_5$ | CH | A | 152–153 |
| 5 | 4-Br—$C_6H_4$ | $C_6H_5$ | CH | A × ½ $CuCl_2$ | 198–200 |
| 6 | 4-Br—$C_6H_4$ | 4-Cl—$C_6H_4$ | CH | A | 143–144 |
| 7 | $C_6H_5$ | 2,4-$Cl_2$—$C_6H_3$ | CH | A | 103 |
| 8 | 4-Br—$C_6H_4$ | 2,4-$Cl_2$—$C_6H_3$ | CH | A | 107–108 |
| 9 | 2,4-$Cl_2$—$C_6H_3$ | 4-Cl—$C_6H_4$ | CH | A | 135 |
| 10 | 4-Cl—$C_6H_4$ | $C_6H_5$ | CH | A | 138 |
| 11 | 4-Br—$C_6H_4$ | 2,4-$Cl_2$—$C_6H_2$ | N | A | 133–134 |
| 12 | $CH_3$ | 2,4-$Cl_2$—$C_6H_3$ | CH | B | 113–117.5 |
| 13 | $CH_3$ | 2,4-$Cl_2$—$C_6H_3$ | CH | A | 98–104 |
| 14 | $C(CH_3)_3$ | 4-Cl—$C_6H_4$ | N | A | 79–80 |
| 15 | $C(CH_3)_3$ | 4-Cl—$C_6H_4$ | CH | A × HCl | 214–216 |
| 16 | $C(CH_3)_3$ | $C_6H_5$ | N | A × HCl | 148 |
| 17 | $C(CH_3)_3$ | $C_6H_5$ | CH | A | 75 |
| 18 | $(CH_3)_3$ | 2,4-$Cl_2$—$C_6H_3$ | N | A | 124 |
| 19 | $C(CH_3)_3$ | 2,4-$Cl_2$—$C_6H_3$ | CH | A | 95 |
| 20 | 4-Cl—$C_6H_4$ | 4-$C(CH_3)_3$—$C_6H_4$ | CH | B | 160–162 |
| 21 | 4-Cl—$C_6H_4$ | 4-$C(CH_3)_3$—$C_6H_4$ | N | A | 176–177 |
| 22 | 2,4-$Cl_2$—$C_6H_3$ | 4-$C(CH_3)_3$—$C_6H_4$ | CH | A | 132–134 |
| 23 | $CH_3$ | 2,4-$Cl_2$—$C_6H_3$ | N | A | 105–108 |
| 24 | $CH_3$ | 2,4-$Cl_2$—$C_6H_3$ | N | B | 80–85 |
| 25 | $CH_3$ | 2,4-$Cl_2$—$C_6H_3$ | N | A:B = 1:1 | 70–81 |
| 26 | 4-$C(CH_3)_3$—$C_6H_4$ | 4-Cl—$C_6H_4$ | CH | A | 100–152 |
| 27 | 4-$C(CH_3)_3$—$C_6H_4$ | 4-Cl—$C_6H_4$ | N | A | 105–107 |
| 28 | 4-$C(CH_3)_3$—$C_6H_4$ | 2,4-$Cl_2$—$C_6H_3$ | CH | A | 101–113 |
| 29 | 4-$C(CH_3)_3$—$C_6H_4$ | 2,4-$Cl_2$—$C_6H_3$ | N | A | 108–111 |
| 30 | 4-Cl—$C_6H_4$ | 3-$OCH_3$—$C_6H_4$ | CH | A × HCl | 173 |
| 31 | 4-Cl—$C_6H_4$ | 3-$OCH_3$—$C_6H_4$ | N | A | 77 |
| 32 | $C_6H_5$ | 2,4-$Cl_2$—$C_6H_3$ | N | A | 159–161 |
| 33 | 4-Cl—$C_6H_4$ | 3-$CF_3$—$C_6H_4$ | CH | A | 101–104 |
| 34 | 4-Cl—$C_6H_4$ | 3-$CF_3$—$C_6H_4$ | N | A | 107–109 |
| 35 | $C_6H_5$ | 3-$CF_3$—$C_6H_4$ | CH | A | 77–78.5 |
| 36 | $C_6H_5$ | 3-$CF_3$—$C_6H_4$ | N | A × HCl | 131–132 |
| 37 | $C_6H_5$ | $C_6H_5$ | CH | A | 108–110 |
| 38 | 4-Cl—$C_6H_4$ | 4-F—$C_6H_4$ | CH | A | 130–132 |
| 39 | $C_6H_5$ | 4-Cl—$C_6H_4$ | CH | A | 105–106 |
| 40 | $C_6H_5$ | $C_6H_5$ | N | A | 116–118 |
| 41 | $C_6H_5$ | 4-Cl—$C_6H_4$ | N | A | 114–115 |
| 42 | 4-Cl—$C_6H_4$ | $C_6H_5$ | N | A | 106–110 |

-continued

| Ex. no. | A | B | Z | Diastereomer | M.p. [°C.] |
|---|---|---|---|---|---|
| 43 | 4-C6H5—C6H4 | 4-Cl—C6H4 | N | A | 163–165 |
| 44 | 4-Br—C6H4 | C6H5 | N | A | 115–120 |
| 45 | 4-Br—C6H4 | 4-Cl—C6H4 | N | A | 115–120 |
| 46 | 4-Cl—C6H4 | 4-F—C6H4 | N | A | 112–117 |
| 47 | 4-Cl—C6H4 | 4-Br—C6H4 | N | A | 115–119 |
| 48 | 4-Cl—C6H4 | 4-Br—C6H4 | CH | A | 114–116 |
| 49 | 4-Cl—C6H4 | 4-Br—C6H4 | CH | B | 179–181 |
| 50 | 2,4-Cl2—C6H3 | 4-Br—C6H4 | CH | A | 135–139 |
| 51 | 43-Cl—C6H4 | 4-F—C6H4 | N | B | 219–223 |
| 52 | 4-Cl—C6H4 | 4-Br—C6H4 | N | B | 210–213 |
| 53 | 2,4-Cl2—C6H3 | 4-Br—C6H4 | N | A | 108–110 |
| 54 | 2,4-Cl2—C6H3 | C6H5 | CH | A | resin |
| 55 | 2,4-Cl2—C6H3 | C6H5 | CH | B | 118–121 |
| 56 | 2,4-Cl2—C6H3 | C6H5 | N | A | resin |
| 57 | 2,4-Cl2—C6H3 | C6H5 | N | B | resin |
| 58 | 4-(SO2—C6H5)—C6H4 | 4-Cl—C6H4 | CH | A | 193–195 |
| 59 | 4-(SO2—C6H5)—C6H4 | 4-Cl—C6H4 | CH | B | 204–205 |
| 60 | 4-(SO2—C6H5)—C6H4 | 4-Cl—C6H4 | N | A | 132–135 |
| 61 | 4-(SO2—C6H5)—C6H4 | 4-Cl2—C6H4 | N | B | 175–177 |
| 62 | 2,4-Cl2—C6H3 | 4-Cl—C6H4 | N | A | |
| 63 | 4-C6H5—C6H4 | 4-Cl—C6H4 | CH | | |
| 64 | 2-Cl—C6H4 | 4-Cl—C6H4 | CH | | |
| 65 | 2-Cl—C6H4 | 4-Cl—C6H4 | N | | |
| 66 | 4-Cl—C6H4 | 3-Cl—C6H4 | CH | | |
| 67 | 4-Cl—C6H4 | 3-Cl—C6H4 | N | | |
| 68 | C6H5 | 3,4-Cl2—C6H3 | CH | | |
| 69 | C6H5 | 3,4-Cl2—C6H3 | N | | |
| 70 | 3,5-Cl2—C6H3 | 4-Cl—C6H4 | CH | | |
| 71 | 3,5-Cl2—C6H3 | 4-Cl—C6H4 | N | | |
| 72 | 2-OCH3—C6H4 | 2,4-Cl2—C6H3 | CH | | |
| 73 | 2-OCH3—C6H4 | 2,4-Cl2—C6H3 | N | | |
| 74 | 3,4-(O—CH2—O)—C6H3 | 4-Br—C6H4 | CH | | |
| 75 | 3,4-(O—CH2—O)—C6H3 | 4-Br—C6H4 | N | | |
| 76 | 4-O—C(CH3)3—C6H4 | 2,4-Cl2—C6H3 | CH | | |
| 77 | 4-O—C(CH3)3—C6H4 | 2,4-Cl2—C6H3 | N | | |
| 78 | 4-CH3—C6H4 | C6H5 | CH | | |
| 79 | 4-CH3—C6H4 | C6H5 | N | | |
| 80 | 4-(O—C6H5)—C6H4 | 4-Br—C6H4 | CH | | |
| 81 | 4-(O—C6H5)—C6H4 | 4-Br—C6H4 | N | | |
| 82 | C6H5 | 4-NO2—C6H4 | CH | | |
| 83 | C6H5 | 4-NO2—C6H4 | N | | |
| 84 | 2-C10H7 | 2,4-Cl2—C6H3 | CH | A | 135 |
| 85 | 2-C10H7 | 2,4-Cl2—C6H3 | N | A | 151 |
| 86 | 4-Cl—C6H4 | 1-CH10H7 | CH | | |
| 87 | 4-Cl—C6H4 | 1-C10H7 | N | | |
| 88 | 4-Cl—C6H4 | 4-Cl—C6H4 | CH | A | 115–120 |
| 89 | 4-Cl—C6H4 | 4-Cl—C6H4 | N | A | 105–108 |
| 90 | 2-C10H7 | 4-Cl—C6H4 | CH | A | 140 |
| 91 | 2-C10H7 | 4-Cl—C6H4 | N | A | 107 |
| 92 | 3,4-Cl2—C6H3 | 4-Br—C6H4 | N | A | 130–134 |
| 93 | 2,4-Cl2—C6H3 | 4-C(CH3)3—C6H4 | CH | B | 142–143 |

The novel compounds, and their salts and metal complex compounds, have an excellent action on a broad spectrum of plant-pathogenic fungi, especially from the Ascomycetes and Basidiomycetes classes. Some of them have a systemic action and may be used as soil and foliar fungicides. They may also be employed for protecting materials.

The fungicidal compounds are of particular interest for combating a large number of fungi in various crops or their seed, especially wheat, rye, barley, oats, rice, Indian corn, cotton, soybeans, coffee, bananas, groundnuts, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, *Erysiphe polygoni* (pr) in beans, *Sphaerotheca pannosa* in roses, *Puccinia* species in cereals, *Rhizoctonia solani* (pr) in cotton, *Helminthosphorium* species in cereals, *Ustilago* species in cereals and sugarcane, *Rhynchosporium secale* in cereals, *Venturia inaequalis* (apple scab), *Botrytis cinerea* in grapes and strawberries, and *Septoria nodorum* in cereals.

The compounds are applied by spraying or dusting the plants, or treating the seed with the active ingredients. Application may be effected before or after infection of the plants or seed by the fungi.

The following wood- and paint-discoloring fungi, soft rot fungi and wood-destroying fungi for instance may be combated with the agents according to the invention: *Aureobasidium pullulans, Sclerophoma pityophila, Ceratocystis spec., Paecilomyces variotii, Hormiscium spec., Stemphylium spec., Fhoma violacea, Cladosporium herbarum, Trichoderma viride, Chaetomium globosum, Humicola grisea, Merulius lacrimans, Coniophora puteana, Lentinus lepideus, Lenzites trabea, Trametes versicolor, Stereum hirsutum*, and *Fomes annosus*.

The novel compounds may be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics. e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt % of active ingredient.

The application rates depend on the effect desired, and range from 0.1 to 3 kg of active ingredient per hectare, or more. The novel compounds may also be used to protect materials, e.g., as fungicides for surface coatings and soft PVC, in which case the application rates are from 0.05 to 5% (by weight) of active ingredient, based on the total weight of the paints to be preserved or the PVC to be microbicidally treated. The novel active ingredients may be applied, for protecting wood, in formulations such as solutions, emulsions, pastes and oil dispersions. These formulations generally contain from 0.1 to 95, and preferably from 0.25 to 50, wt % of active ingredient. The application rates depend on the effect desired, and range from 0.5 to 8 g of active ingredient per $m^2$ of wood surface to be protected, or from 50 to 4,000 $g/m^3$ of wood. Paints contain for instance from 1.5 to 2 wt % of active ingredient. To protect wood-base materials, the active ingredients may be added to the adhesive as an emulsion, or mixed with it, for example in amount of from 2 to 6 wt %.

The active ingredients are applied by painting, spraying, immersion, pressure impregnation, or diffusion.

The agents and the ready-to-use formulations made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of the compound of Example 5 is mixed with 10 parts of weight of N-methyl-alpha-pyrrolidone. A mixture is obtained which is suitable for application in the form of very fine drops.

II. 10 parts by weight of the compound of Example 7 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil. By pouring the solution into water and uniformly distributing it therein, an aqueous dispersion is obtained.

III. 20 parts by weight of the compound of Example 8 is dissolved in a mixture consisting of 60 parts by weight of cyclohexanone, 30 parts by weight of isobutanol, and 10 parts by weight of the adduct of 40 moles of ethylene oxide and 1 mole of castor oil. By pouring the solution into water and finely distributing it therein, an aqueous dispersion is obtained.

IV. 20 parts by weight of the compound of Example 10 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of the compound of Example 14 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of the compound of Example 15 is intimately mixed with 97 parts by weight of particulate kaolin. A dust is obtained containing 3% by weight of the active ingredient.

VII. 30 parts by weight of the compound of Example 16 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 18 is intimately mixed with 10 parts of the sodium salt of a phenolsulfonic acid-urea-formaldehyde condensate, 2 parts of silica gel and 48 parts of water to give a stable aqueous dispersion.

IX. 20 parts of the compound of Example 40 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

X. To prepare an oily wood preservative containing 1 wt % of active ingredient, 1 part (by weight) of compound 42 is dissolved, with slight heating, in 55 parts of a gasoline fraction rich in aromatics. Subsequently, 10 parts of an alkyd resin is added, and the mixture is made up to 100 parts by adding mineral spirit at room temperature.

Oily wood preservatives containing from 0.25 to 5 wt % of active ingredient are prepared similarly.

If desired, water repellants may be added to the oily wood preservatives to give impregnating finishes. Examples of suitable substances are zinc stearate, aluminum stearate, and waxes. Further, particulate inorganic or organic pigments or oil-soluble dyes may be incorporated into the formulations to achieve color effects.

To protect wood against fungus attack, usually from 50 to 200 ml of the oily wood preservatives is applied per $m^2$ of wood surface area by coating, spraying or dipping.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased.

The following list of fungicides, with which the compounds according to the invention may be combined, is intended to illustrate and not to restrict the combination possibilities.

Examples of fungicides which may be combined with the active ingredients according to the invention are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-(1,1,2,2-tetrachloroethylthio)-tetrahydrophthalimide
N-trichloromethylthiotetrahydrophthalimide
2-heptadecyl-2-imidazoline acetate
2,4-dichloro-6-(o-chloroanilino)-s-triazine
0,0-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(b 4,5-b)-quinoxaline
methyl 1-(butylcarbamoyl)-2-benzimidazole carbamate
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as dodecylguanidine acetate
3-[2-(3,5-dimethyl-2-oxycyclohexyl)-2-hydroxyethyl]-glutarimide hexachlorobenzene
N-dichlorofluoromethylthio-N,N'-dimethyl-N-phenylsulfuric acid diamide
D,L-methyl-N-(2,6-dimethylphenyl)-N-(2-furoyl)-alanate
methyl D,L-N-(2,6-dimethylphenyl)-N-(2-methoxyacetyl)-alanate
diisopropyl 5-nitroisophthalate
2,5-dimethylfuran-3-carboxanilide
2-methylbenzoic acid anilide
2-iodobenzoic acid anilide
1-(3,4-dichloroanilino)-formylamino-2,2,2-trichloroethane
2,6-dimethyl-N-tridecylmorpholine and its salts
2,6-dimethyl-N-cyclododecylmorpholine and its salts
1-(1',2',4'-triazolyl-1')-1-(4'-chlorophenoxy)-3,3-dimethylbutan-2-one
1-(1',2',4'-triazolyl-1')-1-(4'-chlorophenoxy)-3,3-dimethyl-butan-2-ol
N-(2,6-dimethylphenyl)-N-chloroacetyl-D,L-2-aminobutyrolactone
N-(n-propyl)-N-(2,4,6-trichlorophenoxyethyl)-N'-imidazolyl urea
N-cyclohexyl-N-methoxy-2,5-dimethylfuran-3-carboxamide
2,4,5-trimethylfuran-3-carboxanilide
5-methyl-5-vinyl-3-(3,5-dichlorophenyl)-2,4-dioxo-b 1,3-oxazolidine
5-methoxymethyl-5-methyl-3-(3,5-dichlorophenyl)-2,4-dioxo-1,3-oxazolidine
N-[3-(p-tert.-butylphenyl)-2-methylpropyl]-cis-2,6-dimethylmorpholine
N-formyl-N-morpholine-2,2,2-trichloroethyl acetal
1-[2-(2,4-dichlorophenyl)-4-ethyl-1,3-dioxolan-2-yl-ethyl]-1H-1,2,4-triazole
2-[2-(2,4-dichlorophenyl)-4-n-propyl-1,3-dioxolan-2-yl-ethyl]-1H-1,2,4-triazole
organotin compounds, such as tributyltin oxide and tributyltin benzoate
methylene bis-thiocyanate
alkyl-dimethyl-benzylammonium chloride
cetyl-pyridinium chloride
chlorinated phenols, such as tetra- and pentachlorophenol
tetrachloroisophthalic acid dinitrile
2-halobenzoic acid anilide
N-cyclohexyl-N-methoxy-2,5-dimethylfuran-3-carboxamide
N,N-dimethyl-N'-phenyl-(N-fluoromethylthio)-sulfamide
N-phenyl-N,N'-dimethyl-N'-fluorodichloromethyl-thiosulfonyl-diamide
methyl benzimidazole-2-carbamate
2-thiocyanomethyl-thiobenzothiazole
copper naphthenate
copper-8-oxyquinoline
alkali metal salts of N-hydroxy-N-cyclohexyldiazenium oxides.

For the experiments described below, the following prior art compounds were employed for comparison purposes:

1-(2,4-dichlorophenyl)-2-(imidazol-1yl)-ethan-1-ol A (French 2,249,616) and
(2,4-dichlorophenyl)-1,2,4-triazol-1-yl-methyl ketone B (German Laid-Open application DE-OS 2,431,407).

EXPERIMENT 1

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (Erysiphe graminis var. tritici). The plants were then placed in a greenhouse at 20° to 22° C. and 75 to 80% relative humidity. The extent of mildew spread was determined after 7 days.

The results show that for example compounds 1, 28, 31, 32, 33, 34, 35, 36, 42, 44 and 46, applied as 0.025, 0.006 and 0.0015% spray liquors, had a better fungicidal action (e.g., 100%) than compounds A and B (e.g., 90%).

EXPERIMENT 2

Action of leaf rust of wheat

Leaves of pot-grown wheat seedlings of the "Jubilar" variety were dusted with spores of rust (Puccinia recondita). The pots were then placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results show that compounds 3, 4, 6, 10, 11, 30, 31, 32, 33, 34, 38, 41, 42, 43, 44 and 46, applied as 0.025, 0.006 and 0.0015% spray liquors, had a better fungicidal action (e.g., 100%) than compounds A and B (e.g., 50%).

EXPERIMENT 3

Action on cucumber mildew

The leaves of pot-grown cucumber mildew seedlings of the "Chinesische Schlange" variety were sprayed at the 2-leaf stage with a spore suspension of cucumber mildew (Erysiphe cichoracearum). After about 20 hours, the plants were sprayed to runoff with aqueous emulsions consisting (dry basis) of 80% of active ingredient and 20% of emulsifier. After the sprayed-on layer had dried, the plants were set up in the greenhouse at from 20° to 22° C. and a relative humidity of 70 to 80%. To assess the action of the novel compounds, the extent of fungus spread was determined after 21 days.

The results show that for example compounds 1, 4, 6, 10, 11, 12, 14, 15, 18, 19, 28, 31, 32, 34, 36, 38, 40, 41, 42, 43, 44 and 45, applied as 0.025 spray liquors, had a good fungicidal action (e.g., 100%).

EXPERIMENT 4

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results show that for instance compounds 1, 3, 4, 6, 10, 11, 12, 19, 30, 31, 32, 33, 35, 36, 37, 38, 39, 40, 42, 44 and 46, applied as 0.05% spray liquors, had a better fungicidal action (e.g., 97%) than compounds A and B (e.g., 70%).

EXPERIMENT 5

Filter paper discs 13 mm in diameter and 1 mm thick were impregnated with 0.2 ml of solutions each containing 200 parts of active ingredient per million parts of solution (ppm). The discs were then placed on a 2% malt extract agar in glass dishes (with lid) which had previously been inoculated with spores of the wood-discoloring fungus Pullularia pullulans. The dishes were then incubated for 3 days at from 22° to 24° C. After this time, the fungi in the control dishes had spread very well; the fungicidal action of the active ingredients was assessed in the following manner from the fungus-free ones (halos) which had formed round the filter paper:

−no halo (no fungicidal action)

+halo less than 2 mm in width (slight fungicidal action)

++average halo from 2 to 6 mm in width (good fungicidal action)

+++halo wider than 6 mm (excellent fungicidal action)

| Active ingredient | Action on Pullularia pullulans |
|---|---|
| 22 | +++ |
| 42 | +++ |
| 50 | +++ |
| Control | − |

EXPERIMENT 6

The compounds were dissolved in acetone, and 40 ppm of these solutions were added to a liquefied malt extract agar. The agar was poured into Petri dishes and, after it had solidified, the fungicide-containing agar was centrally inoculated with mycelium of the wood-destroying fungi Comophora puteana and Trametes versicolor; of the soft-rot and mildew fungus *Chaetomium globosum;* and with spores of the saprophyte wood fungus Trichoderma viride.

After the dishes had been incubated for 5 days at 25° C., the development of the fungus colonies on the nutrient medium was assessed against the control (no active ingredient):

0=no fungus growth (fungus mycelium killed)

1=slight fungus growth (up to ⅓ of the agar surface covered)

3=average fungus growth (up to ⅔ of the agar surface covered)

5=uncontrolled fungus growth (surface of agar completely covered)

| Active ingredient no. | Action on | | | |
|---|---|---|---|---|
| | Coniophora puteana | Trametes versicolor | Chaetomium globosum | Trichoderma viride |
| 10 | 0 | 0 | 0 | 0 |
| 14 | 0 | 0 | 0 | 0 |
| 15 | 0 | 0 | 3 | 1 |
| 22 | 1 | 0 | 1 | 1 |
| 23 | 0 | 0 | 0 | 0 |
| 42 | 0 | 0 | 0 | 0 |
| 44 | 0 | 0 | 1 | 0 |
| 45 | 0 | 0 | 1 | 0 |
| 46 | 0 | 0 | 0 | 0 |
| 48 | 0 | 0 | 0 | 0 |
| 49 | 0 | 0 | 1 | 0 |
| 50 | 0 | 0 | 0 | 0 |
| Control (no active ingredient) | 5 | 5 | 5 | 5 |

We claim:

1. A fungicidal composition containing as an active agent from 0.1 to 95 weight percent of an azolylmethyloxirane of the formula

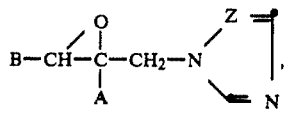
(I)

where A and B are identical or different and independently of one another are each alkyl of 1 to 4 carbon atoms, naphthyl, biphenyl or phenyl, and the phenyl radical can be substituted by halogen or nitro, or by alkyl, alkoxy or haloalkyl, each of 1 to 4 carbon atoms, or by phenoxy or phenylsulfonyl, and Z is CH or N, or a plant-tolerated addition salt or metal complex thereof, and a solid or liquid inert additive.

2. A fungicidal composition as set forth in claim 1, where A and B are phenyl or phenyl substituted by halogen or trifluoromethyl.

3. A process for combating fungi, wherein an effective amount of an azolylmethyloxirane of the formula

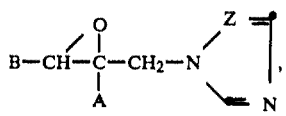
(I)

where A and B are identical or different and independently of one another are each alkyl of 1 to 4 carbon atoms, naphthyl, biphenyl or phenyl, and the phenyl radical can be substituted by halogen or nitro, or by alkyl, alkoxy or haloalkyl, each of 1 to 4 carbon atoms, or by phenoxy or phenylsulfonyl, and Z is CH or N, or a plant-tolerated addition salt or metal complex thereof, is applied to the fungi, or on materials, areas, plants or seed threatened by fungus attack.

* * * * *